(12) United States Patent
Prasad et al.

(10) Patent No.: US 12,741,104 B2
(45) Date of Patent: Sep. 22, 2026

(54) REUSE PREVENTION FLUSH SYRINGE

(71) Applicant: Becton, Dickinson and Company, Franklin Lakes, NJ (US)

(72) Inventors: Shishir Prasad, Ramsey, NJ (US); Praveen Nalawade, Belagavi (IN); Manish Kumar, Bengaluru (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 931 days.

(21) Appl. No.: 17/982,115

(22) Filed: Nov. 7, 2022

(65) Prior Publication Data

US 2024/0148986 A1 May 9, 2024

(51) Int. Cl.
*A61M 5/50* (2006.01)
*A61M 5/31* (2006.01)
*A61M 5/315* (2006.01)

(52) U.S. Cl.
CPC ........ *A61M 5/5066* (2013.01); *A61M 5/3129* (2013.01); *A61M 5/31511* (2013.01); *A61M 2005/5073* (2013.01)

(58) Field of Classification Search
CPC ........ A61M 5/5066; A61M 2005/5073; A61M 5/31511; A61M 5/5013; A61M 5/347; A61M 2005/5026
See application file for complete search history.

(56) References Cited

U.S. PATENT DOCUMENTS 2,842,124 A * 7/1958 James ................. A61M 39/223 417/63
4,699,614 A * 10/1987 Glazier ............... A61M 5/5066 604/110
5,533,970 A * 7/1996 Berger .................. A61M 5/322 604/110
8,075,523 B2 12/2011 Wayman et al.
10,426,901 B2 10/2019 Cho
2011/0106016 A1* 5/2011 Wei ..................... A61M 5/2466 604/201
2014/0171875 A1 6/2014 Poncon
2016/0250415 A1* 9/2016 Yagi .................. A61M 39/1011 604/187
2018/0296774 A1 10/2018 Cho
2019/0167911 A1* 6/2019 Rassouli ............... A61M 5/345
(Continued)

FOREIGN PATENT DOCUMENTS

WO 2022185313 A1 9/2022

*Primary Examiner* — Theodore J Stigell
(74) *Attorney, Agent, or Firm* — Servilla Whitney LLC

(57) ABSTRACT

A syringe includes a barrel having first and second ends, with the barrel defining an interior space and a stopper positioned therein, the stopper moveable within the interior space relative to the barrel, a plunger connected to the stopper, and a collar having threads configured to engage threads of a medical connector. The collar is at least partially received by the barrel, with one of the barrel and the collar defining a slot and the other of the barrel and the collar having a pin received within the slot. The collar has a connection position where the collar is fixed relative to the barrel when the syringe is being connected to the medical connector, a disconnection position where the collar is fixed relative to the barrel when the syringe is being disconnected from the medical connector, and a reuse prevention position wherein the collar is rotatable relative to the barrel.

15 Claims, 11 Drawing Sheets

(56) References Cited

U.S. PATENT DOCUMENTS

2020/0405963 A1* 12/2020 Combes ............ A61M 5/31513
2021/0260356 A1* 8/2021 Mummert ........... A61M 5/3134
2022/0032029 A1 2/2022 Lazzara et al.

* cited by examiner

REUSE PREVENTION FLUSH SYRINGE

BACKGROUND OF THE INVENTION

Field of the Invention

The present disclosure relates generally to a flush syringe with a reuse prevention feature.

Description of Related Art

Prefilled flush syringes are used to flush intravenous lines and medical connectors or components. Reuse of prefilled flush syringes for multiple patients is an unsafe practice that can lead to contamination and transmission of pathogens. Reuse of prefilled flush syringes on the same patient may also present problems. A large volume prefilled flush syringe, such as a 10 mL syringe, may be used multiple times during a procedure. Multiple connections and disconnections, even with a single patient, can lead to contamination and injections. Many hospital stock 10 mL prefilled flush syringes due to their efficiency and effectiveness for flushing all sizes of intravenous devices. Such prefilled flush syringes are reused, especially for short peripheral catheters, because the flushing procedure only uses 3-5 mL to flush before and after an intravenous push of medications.

SUMMARY OF THE INVENTION

In one aspect or embodiment, a syringe includes a barrel having a first end and a second end positioned opposite from the first end, with the barrel defining an interior space, a stopper positioned within the interior space, with the stopper moveable within the interior space relative to the barrel, a plunger connected to the stopper, and a collar having threads configured to engage corresponding threads of a medical connector. The collar is at least partially received by the barrel. One of the barrel and the collar defines a slot and the other of the barrel, and the collar includes a pin received within the slot. The collar has a connection position where the collar is fixed relative to the barrel when the syringe is being connected to the medical connector, a disconnection position where the collar is fixed relative to the barrel when the syringe is being disconnected from the medical connector, and a reuse prevention position where the collar is rotatable relative to the barrel.

The slot of the barrel may include a connection portion having a first end and a second end and a reuse prevention portion extending from the connection portion, where the pin is positioned at the first end of the connection portion of the slot and engaged with the barrel when the collar is in the connection position, where the pin is positioned at the second end of the connection portion of the slot and engaged with the barrel when the collar is in the disconnection position, and where the pin is positioned within the reuse prevention portion of the slot when the collar is in the reuse prevention position. The reuse prevention portion of the slot may extend 360 degrees. The slot may include a transition portion extending between the connection portion and the reuse prevention portion of the slot.

The barrel may include a protrusion extending into the connection portion of the slot, where the protrusion is configured to allow movement of the pin from the first end of the connection portion of the slot to the second end of the connection portion of the slot and prevent movement of the pin from the second end of the connection portion of the slot to the first end of the connection portion of the slot. The protrusion may be configured to guide the pin toward the reuse prevention portion of the slot. The connection portion of the slot may extend in a radial direction relative to a longitudinal axis of the barrel, where the protrusion is flexible and extends into the connection portion of the slot in a direction extending from the first end of the connection portion of the slot toward the second end of the connection portion of the slot. The collar may be configured to move axially toward the second end of the barrel when the collar moves from the disconnection position to the reuse prevention position. The barrel may define the slot and the collar may include the pin.

The barrel may define an opening extending from the first end of the barrel to the slot, with the opening configured to receive the pin during assembly of the collar within the barrel. The opening may include a narrowed portion, where the pin is configured to widen the opening when the pin engages the narrowed portion and subsequently return to an original position when the pin enters the slot. The syringe may further include a cap positioned on the first end of the barrel, where the cap comprises an extension received within the opening of the barrel to secure the cap to the barrel.

An inner surface of the collar may be threaded. The barrel may include a male luer received within the collar.

In a further aspect or embodiment, a syringe includes a barrel having a first end and a second end positioned opposite from the first end, with the barrel defining an interior space, a stopper positioned within the interior space, with the stopper is moveable within the interior space relative to the barrel, a plunger connected to the stopper, and a collar including threads configured to engage corresponding threads of a medical connector, with the collar at least partially received by the barrel. One of the barrel and the collar defines a slot and the other of the barrel and the collar including a pin received within the slot, where the collar has a connection position where the collar is fixed relative to the barrel when the syringe is being connected to the medical connector, a disconnection position where the collar is fixed relative to the barrel when the syringe is being disconnected from the medical connector, and a reuse prevention position wherein the collar is axially spaced from the first end of the barrel to prevent the threads of the collar from engaging with the threads of the medical connector.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

DETAILED DESCRIPTION

Figure 1:
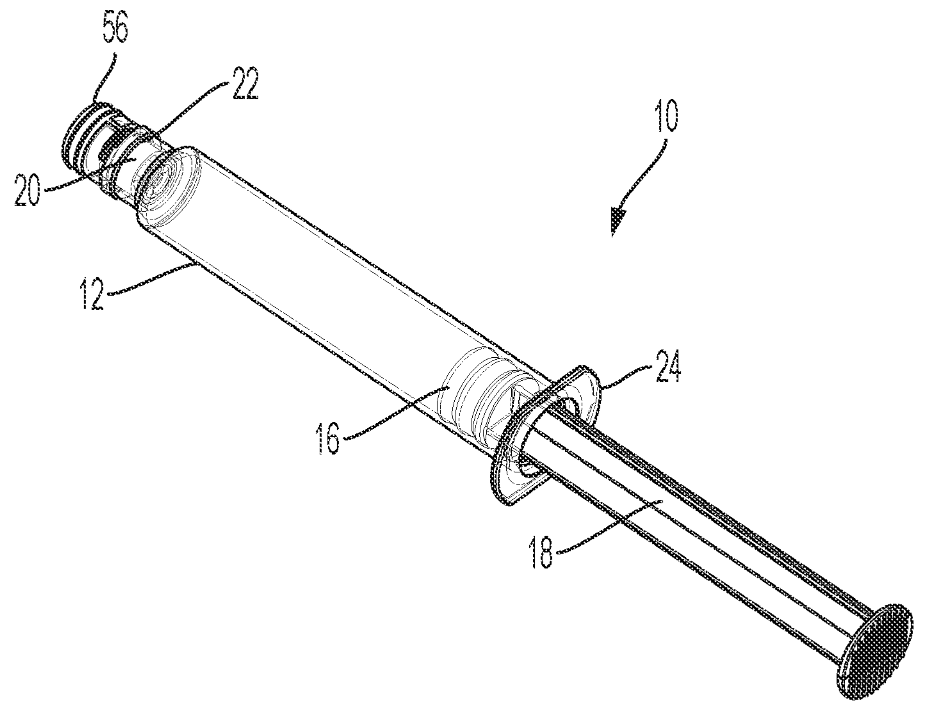
FIG. 1 is a perspective view of a flush syringe according to one aspect of the present invention.
Figure 2:
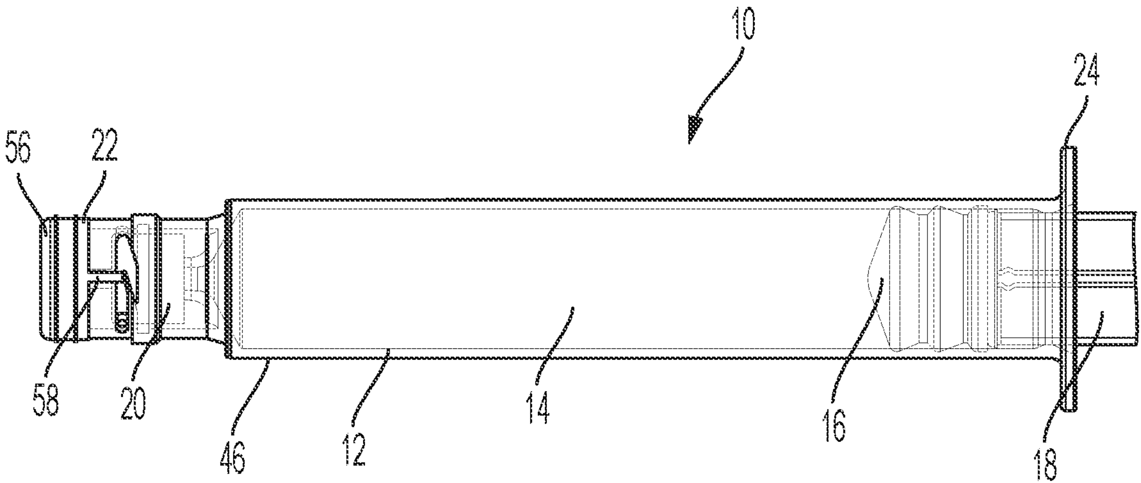
FIG. 2 is a partial side view of the flush syringe of FIG. 1.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1-21, according to one aspect of present application, a syringe 10 includes a barrel 12 defining an interior space 14, a stopper 16 positioned within the interior space 14, a plunger 18 connected to the stopper 16, and a collar 20 at least partially received by the barrel 12. The barrel 12 has a first end 22 and a second end 24 positioned opposite from the first end 22. The stopper 16 is moveable within the interior space 14 relative to the barrel 12. The collar 20 includes threads 26 configured to engage corresponding threads 28 of a medical connector 30. One of the barrel 12 and the collar 20 defines a slot 32 and the other of the barrel 12 and the collar 20 includes a pin 34 received within the slot 32. The collar 20 has a connection position (FIGS. 3 and 13) where the collar 20 is fixed relative to the barrel 12 when the syringe 10 is being connected to the medical connector 30, a disconnection position (FIGS. 6 and 15) where the collar 20 is fixed relative to the barrel 12 when the syringe 10 is being disconnected from the medical connector 30, and a reuse prevention position (FIGS. 9 and 19) where the collar 20 is rotatable relative to the barrel 12. As shown, the barrel 12 defines the slot 32 and the collar 20 includes the pin 34, although the barrel 12 may include the slot 32 and the collar 20 may define the slot 32.

In one aspect or embodiment, the syringe 10 is a prefilled flush syringe. The syringe 10 can be used to dispense a fluid from the barrel 12 by pressing the plunger 18 to move the stopper 16 within the barrel 12 to dispense fluid from the barrel 12. The syringe 10 is configured to be used or connected to the medical connector 30 only once, with the collar 20 moving to the reuse disconnection position upon disconnection of the syringe 10 from the medical connector 30, thereby preventing reuse of the syringe 10 that can lead to contamination and transmission of pathogens. In one aspect or embodiment, the medical connector 30 is a needle-free connector or catheter adapter, although the syringe 10 may be configured to be connected to other suitable medical connectors. As discussed in more detail below, the collar 20 being fixed relative to the barrel 12 when in the connection and disconnection positions (and rotating the barrel 12 to connect or disconnect) allows the syringe 10 to be connected and removed via the threads 26 of the collar 20 from the medical connector 30. However, the collar 20 being free to rotate relative to the barrel 12, when in the reuse prevention position, prevents the syringe 10 from being connected to the medical connector 30 via the collar 20.

Figure 3:
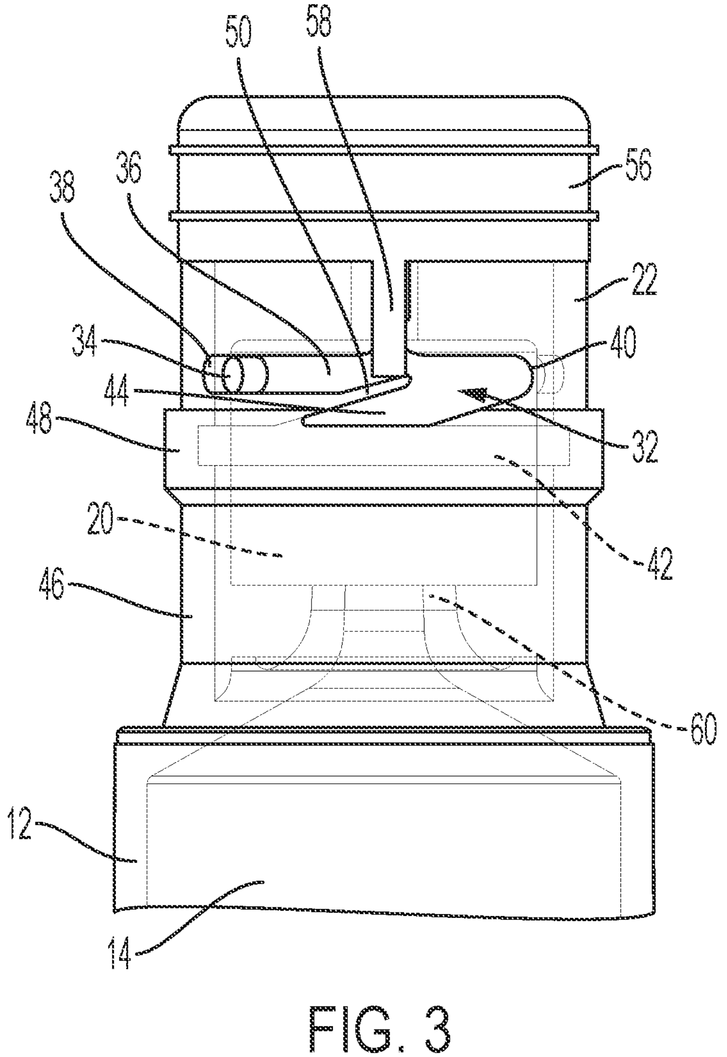
FIG. 3 is a partial side view of the flush syringe of FIG. 1, showing a pre-use position of the flush syringe.
Figure 4:
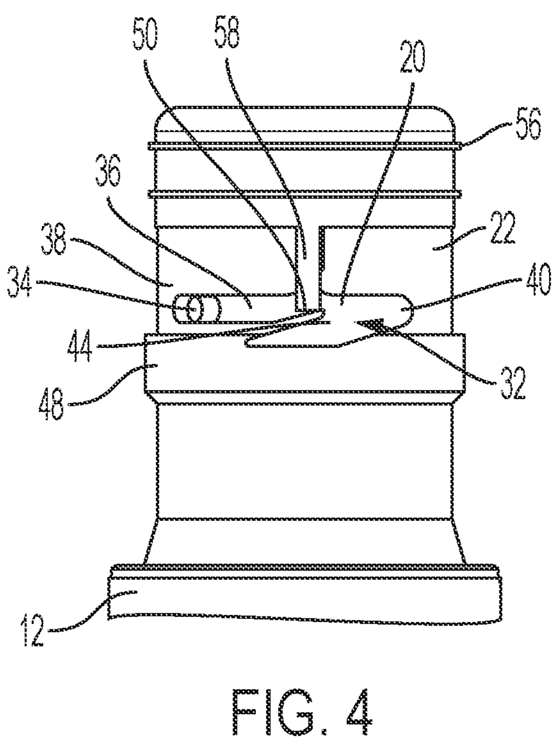
FIG. 4 is a partial side view of the flush syringe of FIG. 1, showing a connection position of a collar.
Figure 5:
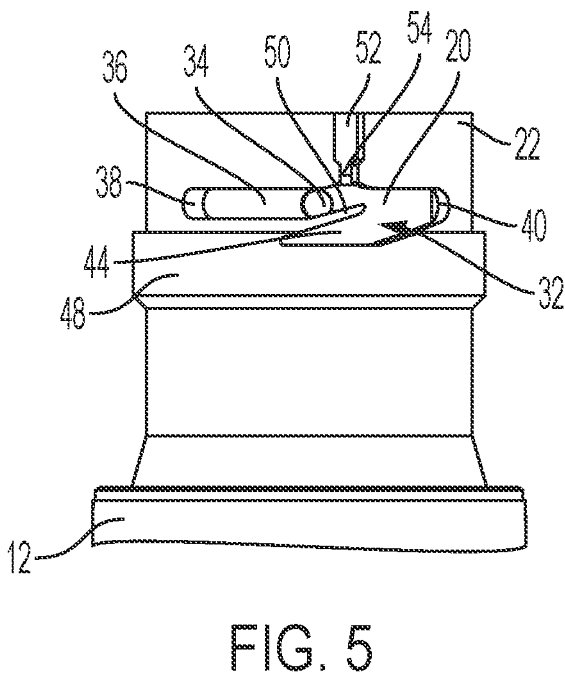
FIG. 5 is a partial side view of the flush syringe of FIG. 1, showing movement of a collar from connection position to a disconnection position.
Figure 6:
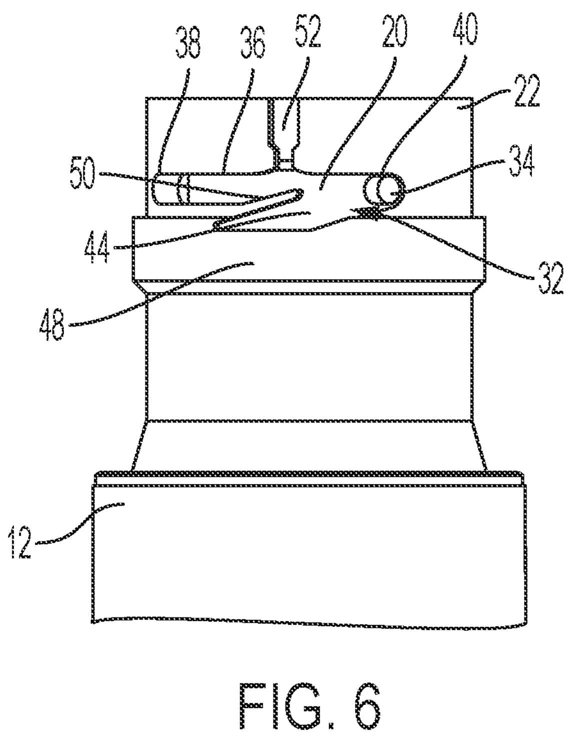
FIG. 6 is a partial side view of the flush syringe of FIG. 1, showing a disconnection position of a collar.
Figure 7:
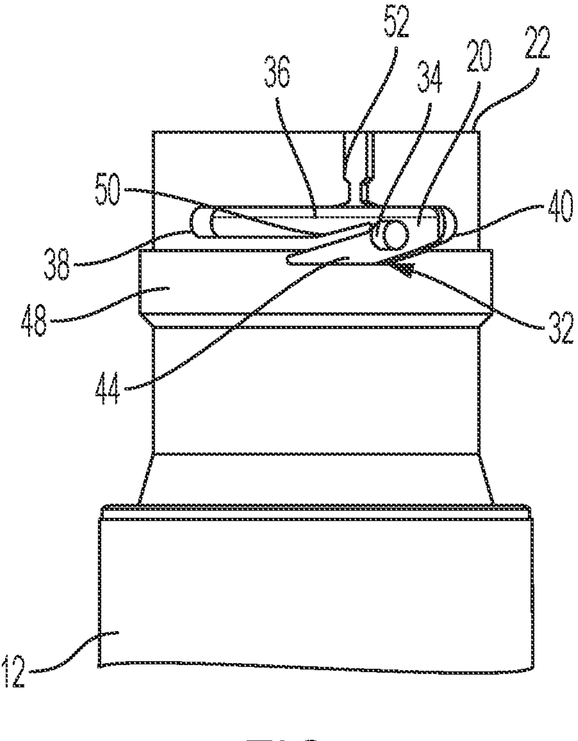
FIG. 7 is a partial side view of the flush syringe of FIG. 1, showing movement of a collar from a disconnection position to a reuse prevention position.
Figures 8, 9:
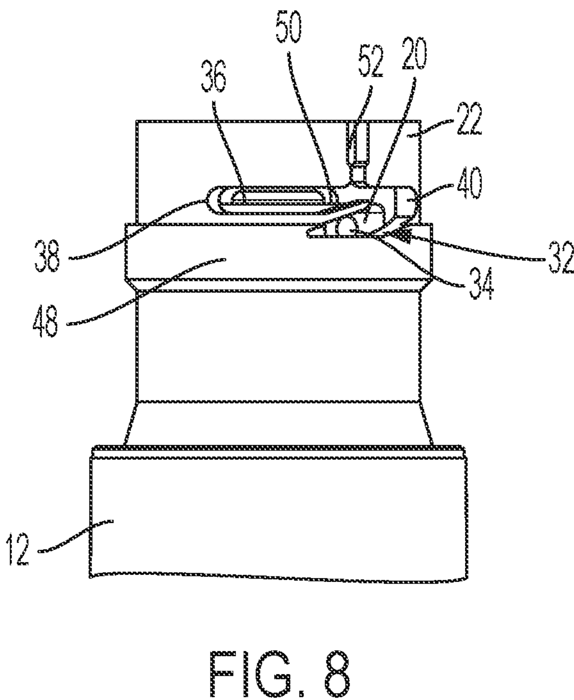
FIG. 8 is a partial side view of the flush syringe of FIG. 1, showing a reuse prevention position of a collar.
FIG. 9 is a partial side view of the flush syringe of FIG. 1, showing a reuse prevention position of a collar with a barrel shown transparent for clarity.

Referring to FIGS. 3, 6, and 9, the slot 32 of the barrel 12 includes a connection portion 36 having a first end 38 and a second end 40 and a reuse prevention portion 42 extending from the connection portion 36. As shown in FIG. 3, the pin 34 is positioned at the first end 38 of the connection portion 36 of the slot 32 and engaged with the barrel 12 when the collar 20 is in the connection position. As shown in FIG. 6, the pin 34 is positioned at the second end 40 of the connection portion 36 of the slot 32 and engaged with the barrel 12 when the collar 20 is in the disconnection position. As shown in FIG. 9, the pin 34 is positioned within the reuse prevention portion 42 of the slot 32 when the collar 20 is in the reuse prevention position. In some aspects, the reuse prevention portion 42 of the slot 32 extends 360 degrees. The slot 32 includes a transition portion 44 extending between the connection portion 36 and the reuse prevention portion 42 of the slot 32. The connection portion 36 of the slot 32 extends entirely through a sidewall 46 of the barrel 12, and the reuse prevention portion 42 of the slot 32 is defined by a protruding portion 48 of the sidewall 46 of the barrel 12. The reuse prevention portion 42 of the slot 32 is closed or not open to an outer surface of the barrel 12.

Referring to FIGS. 3-8, the barrel 12 includes a protrusion 50 extending into the connection portion 36 of the slot 32, with the protrusion 50 configured to allow movement of the pin 34 from the first end 38 of the connection portion 36 of the slot 32 to the second end 40 of the connection portion 36 of the slot 32 and prevent movement of the pin 34 from the second end 40 of the connection portion 36 of the slot 32 to the first end 38 of the connection portion 36 of the slot 32, as discussed in more detail below. The protrusion 50 is configured to guide the pin 34 toward the reuse prevention portion 42 of the slot 32. The connection portion 36 of the slot 32 extends in a radial direction relative to a longitudinal axis of the barrel 12. The reuse prevention portion 42 of the slot 32 also extends in a radial direction relative to a longitudinal axis of the barrel 12. In some aspects or embodiments, the protrusion 50 is flexible and extends into the connection portion 36 of the slot 32 in a direction extending from the first end 38 of the connection portion 36 of the slot 32 toward the second end 40 of the connection portion 36 of the slot 32. The protrusion 50 is angled relative to the connection portion 36 of the slot 32 and is configured to form a one-way path that allows the pin 34 to move to the second end 40 of the connection portion 36, but not from the second end 40 to the first end 38 of the connection portion 36.

In some aspects or embodiments, the pin 34 engages and deflects the protrusion 50 toward the second end 24 of the barrel 12 when moving toward the second end 40 of the connection portion 36 of the slot 32, with the pin 34 engaging and deflecting the protrusion 50 toward the first end 22 of barrel 12 when moving from the second end 40 toward the first end 38 of the connection portion 36 of the slot 32. The protrusion 50 deflecting toward the first end 22 of the barrel 12 blocks or closes the connection portion 36 of the slot 32 to prevent the pin 34 from moving to the first end 38 of the connection portion 36 and guides the pin 34 toward the reuse prevention portion. The pin 34 is cylindrical, although other suitable shapes and configurations may be utilized. A width of the connection portion 36 of the slot 32 and/or a width of the reuse prevention portion 42 of the slot 32 may be the same or slightly larger than a diameter of the pin 34.

Figure 20:
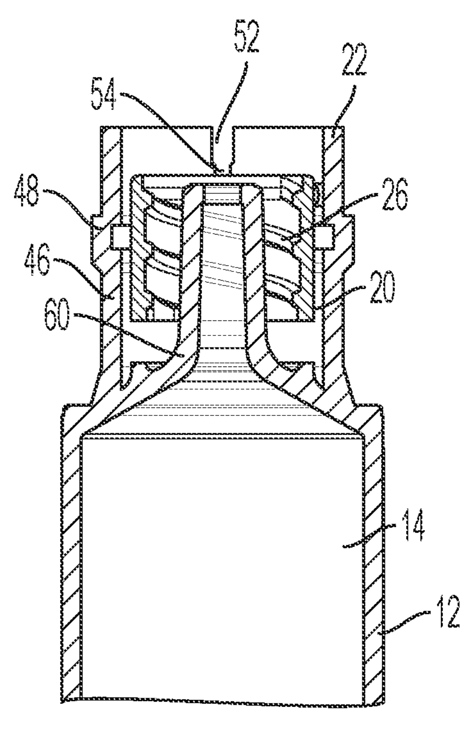
FIG. 20 is a partial cross-sectional view of the flush syringe of FIG. 1, showing a collar in a connection and disconnection positions.
Figure 21:
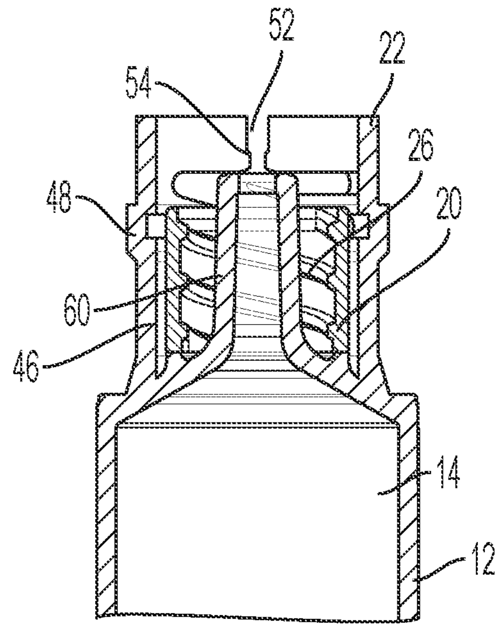
FIG. 21 is a partial cross-sectional view of the flush syringe of FIG. 1, showing a collar in a reuse prevention position.

Referring to FIGS. 20 and 21, the collar 20 is configured to move axially toward the second end 24 of the barrel 12 when the collar 20 moves from the disconnection position to the reuse prevention position. In some aspects or embodiments, the axial movement of the collar 20 when moving to the reuse prevention position is sufficient to prevent the corresponding threads 28 of the medical connector 30 from engaging the threads 26 of the collar 20. The free rotation of the collar 20 relative to the barrel 12 and/or the axial movement of the collar 20 may prevent the reuse of the syringe 10 by inhibiting connection of the medical connector 30 to the syringe 10.

Figure 10:
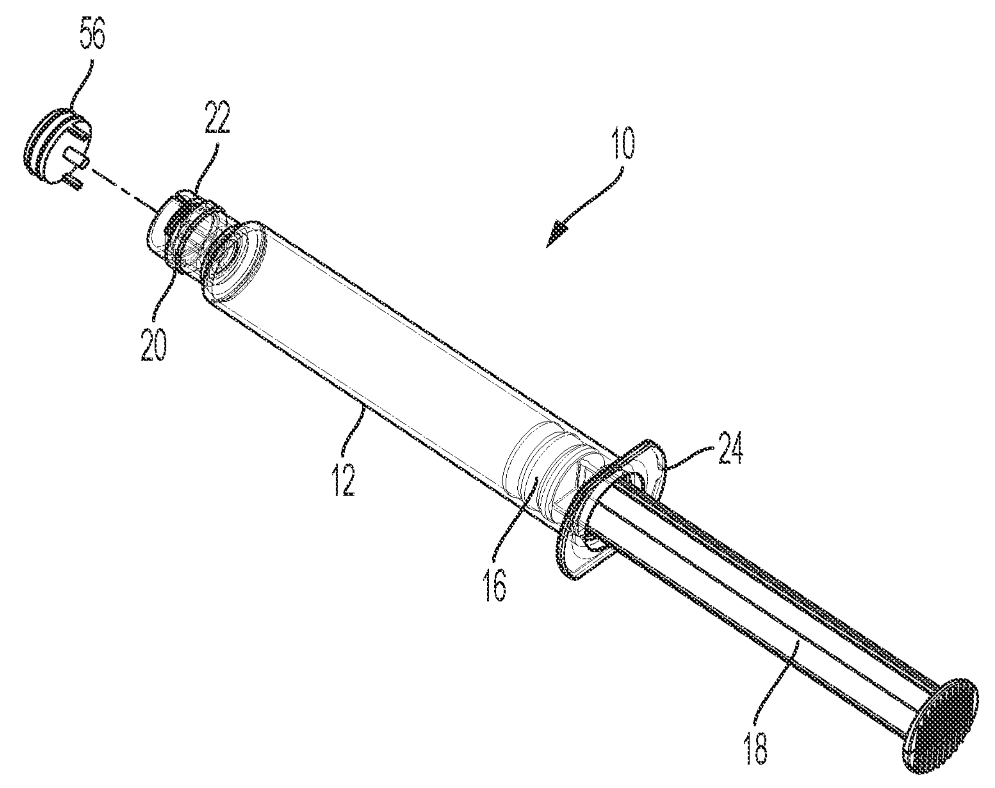
FIG. 10 is a perspective view of the flush syringe of FIG. 1, showing removal of a cap.

Referring to FIGS. 4, 5, 10, and 11, the barrel 12 defines an opening 52 extending from the first end 22 of the barrel 12 to the slot 32. The opening 52 is configured to receive the pin 34 during assembly of the collar 20 within the barrel 12. The opening 52 includes a narrowed portion 54, with the pin 34 configured to widen the opening 52 when the pin 34 engages the narrowed portion 54 and subsequently return to an original position when the pin 34 enters the slot 32. In other words, during assembly of the syringe 10, the pin 34 of the collar 20 can be aligned with the opening 52 and the collar 20 inserted into the first end 22 of the barrel 12 such that the pin 34 pushes through the narrowed portion 54 of the opening 52 to expand the opening 52, with the pin 34 entering the connection portion 36 of the slot 32. Once the pin 34 is in the slot 32, the opening 52 closes or returns to an unbiased state, and the narrowed portion 54 of the opening 52 retains or prevents the pin 34 from exiting the opening 52 to secure the collar 20 within the barrel 12. In some aspects or embodiments, the syringe 10 includes a cap 56 positioned on the first end 22 of the barrel 12. The cap 56 is configured to be removed from the barrel 12 prior to use of the syringe 10 and maintains the sterility and/or creates a fluid tight seal with the barrel 12 to prevent fluid from leaking from the barrel 12. The cap 56 includes an extension 58 received within the opening 52 of the barrel 12 to secure the cap 56 to the barrel 12. As shown in FIG. 10, the cap 56 may include two extensions 58 received by two openings 52 of the barrel 12. The extension(s) 58 may form a snap fit with the barrel 12 to secure the cap 56 to the barrel 12. The syringe 10 may include one or more pins 34 received by one or more slots 32.

In some aspects or embodiments, the collar 20 is annular and the threads 26 are provided on an inner surface of the collar 20. The barrel 12 includes a male luer 60 configured to mate with a corresponding female luer (not shown) of the medical connector 30. The male luer 60 is received within the collar 20 and is in fluid communication with the interior space 14 of the barrel 12.

Figure 11:
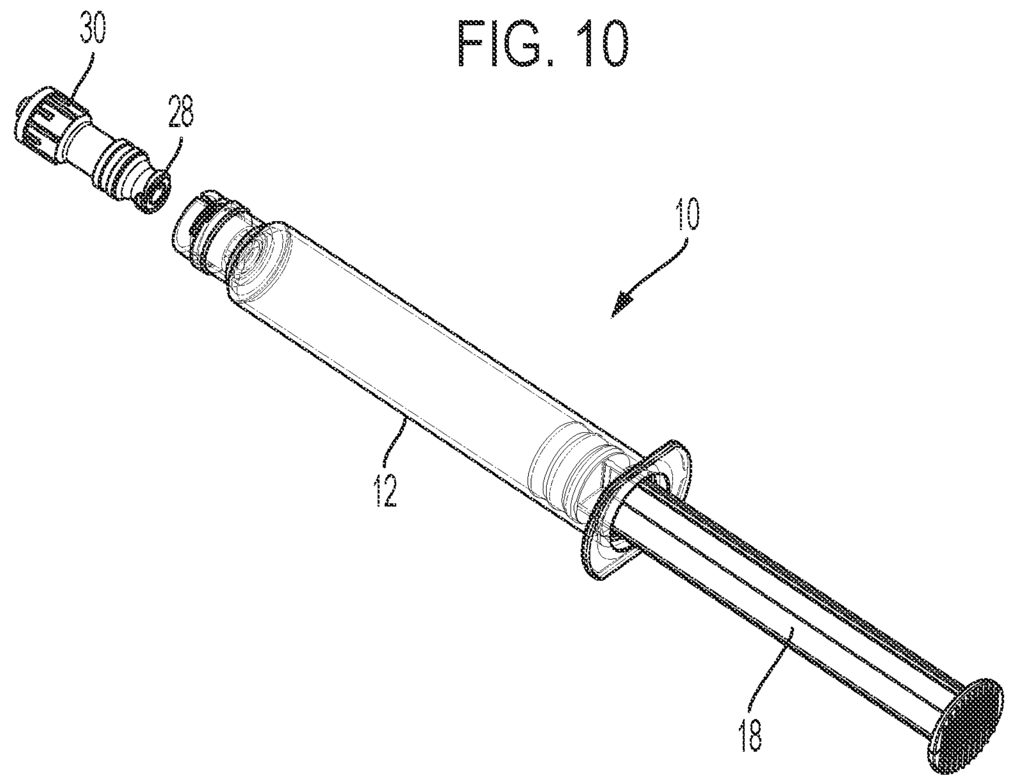
FIG. 11 is a perspective view of the flush syringe of FIG. 1, showing connection to a medical connector.
Figure 12:
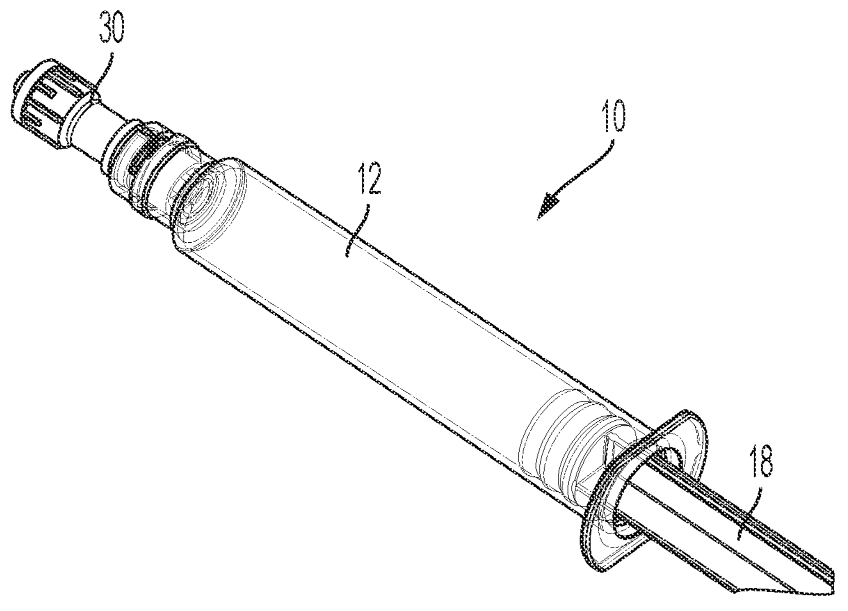
FIG. 12 is a partial perspective view of the flush syringe of FIG. 1, showing a medical connector connected to the flush syringe.
Figure 13:
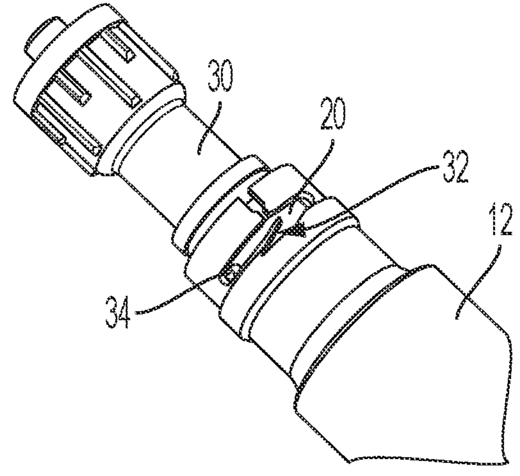
FIG. 13 is an enlarged partial perspective view of the flush syringe of FIG. 1, showing a medical connector connected to the flush syringe.
Figure 14:
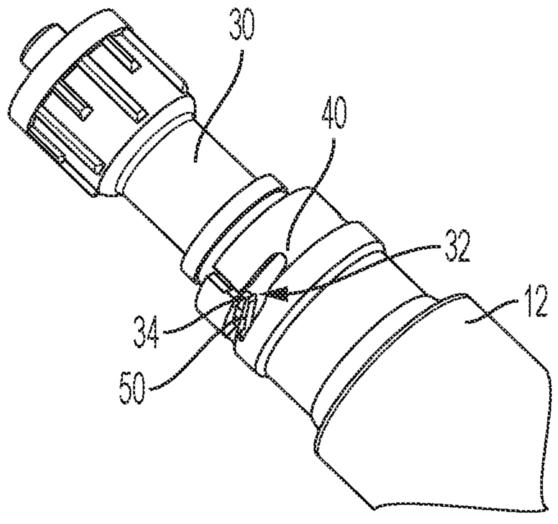
FIG. 14 is an enlarged partial perspective view of the flush syringe of FIG. 1, showing a medical connector being disconnected from the flush syringe.

Referring to FIGS. 10-19, the connection of the syringe 10 to the medical connector 30 and subsequent attempt to reuse the syringe 10 is shown. As shown in FIG. 10, the cap 56 is removed from the barrel 12 prior to use of the syringe 10 by pulling the cap 56 away from the barrel 12 such that the extension(s) 58 release from the barrel 12. As shown in FIGS. 11-13, the medical connector 30 is aligned with the first end 22 of the barrel 12 and the medical connector 30 is inserted into the first end 22 of the barrel 12. The syringe 10 is rotated clockwise relative to the medical connector 30 such that the threads 26 of the collar 20 are engaged with complementary threads 28 of the medical connector 30. The male luer 60 is also received by a female luer of the medical connector 30. As the syringe 10 is rotated, the pin 34 is engaged with the barrel 12 and positioned at the first end 38 of the connection portion 36 of the slot 32, which fixes the collar 20 relative to the barrel 12 during clockwise rotation of the barrel 12 such that the collar 20 and barrel 12 can be threaded onto the medical connector 30. As shown in FIG. 14, to disconnect the syringe 10 from the medical connector 30, the barrel 12 is rotated anti-clockwise relative to the medical connector 30 such that the pin 34 moves from the connection position to the disconnection position. The barrel 12 rotates relative to the collar 20 due to the collar 20 being connected to the medical connector 30 via the threads 26 such that the pin 34 pushes past the protrusion 50 to the second end 40 of the connection portion 36 of the slot 32.

Figure 15:
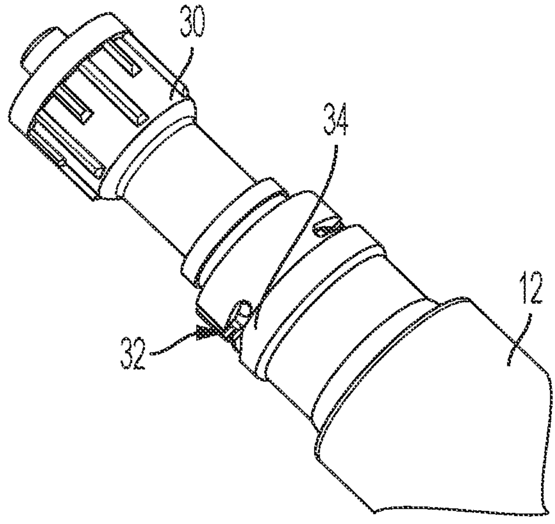
FIG. 15 is an enlarged partial perspective view of the flush syringe of FIG. 1, showing a medical connector being disconnected from the flush syringe.
Figure 16:
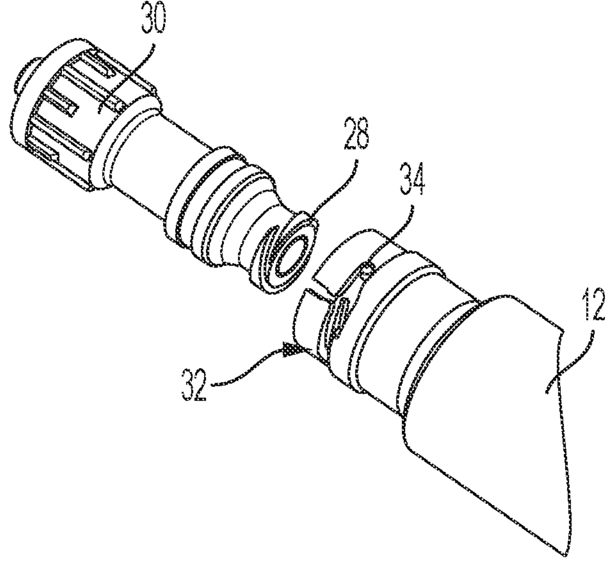
FIG. 16 is an enlarged partial perspective view of the flush syringe of FIG. 1, showing a medical connector disconnected from the flush syringe.
Figure 17:
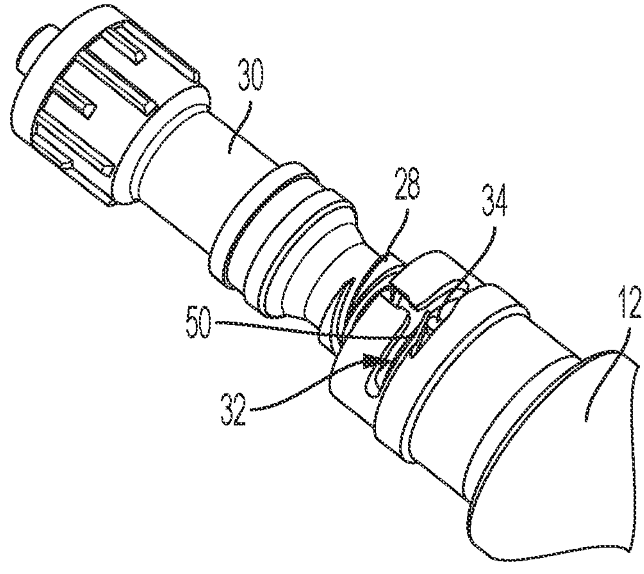
FIG. 17 is an enlarged partial perspective view of the flush syringe of FIG. 1, showing an attempt to reconnect a medical connector to the flush syringe.
Figure 18:
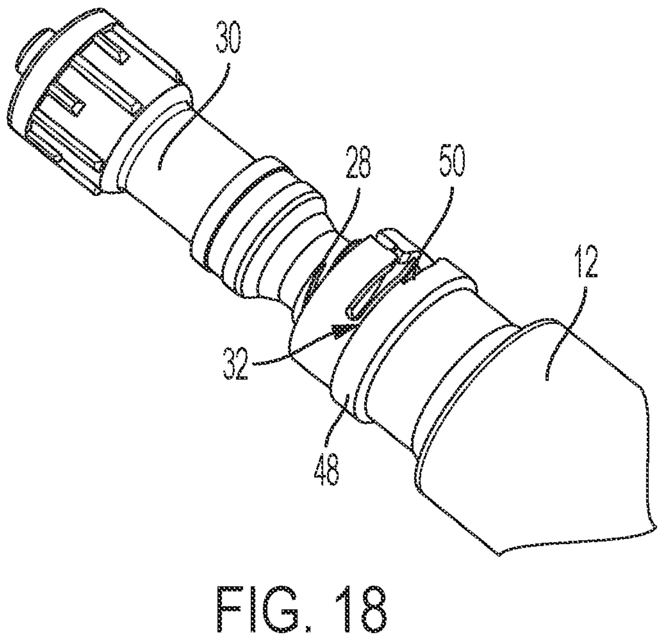
FIG. 18 is an enlarged partial perspective view of the flush syringe of FIG. 1, showing an attempt to reconnect a medical connector to the flush syringe.
Figure 19:
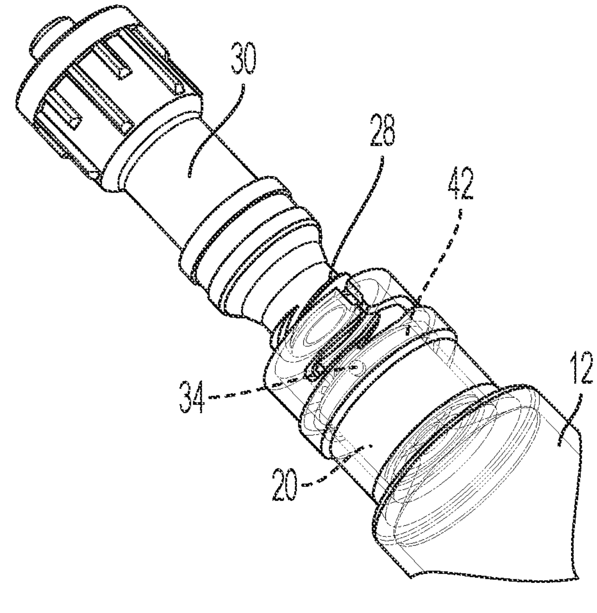
FIG. 19 is an enlarged partial perspective view of the flush syringe of FIG. 1, showing an attempt to reconnect a medical connector to the flush syringe with a barrel shown transparent for clarity.

As shown in FIGS. 15 and 16, with the collar 20 in the disconnection position, the pin 34 is engaged with the barrel 12 at the second end 40 of the connection portion 36 of the slot 32 to fix the collar 20 relative to barrel 12 during anti-clockwise rotation of the barrel 12 such that the collar 20 can be unthreaded from the medical connector 30. As shown in FIGS. 17-19, during an attempt to reconnect the syringe 10 to the medical connector 30, the barrel 12 is again rotated clockwise to thread the collar 20 onto the corresponding threads of the medical connector 30. During such attempt, the collar 20 moves relative to the barrel 12 such that the pin 34 moves within the slot 32 back toward the first end 38 of the connection portion 36 of the slot 32. The protrusion 50, however, prevents the pin 34 from moving to the first end 38 of the connection portion 36 such that the pin

34 engages the protrusion 50 and moves the collar 20 to the reuse prevention position, with the pin 34 moved within the reuse prevention portion 42 of the slot 32. With the pin 34 positioned within the reuse prevention portion 42 of the slot 32, the collar 20 is free to rotate relative to the barrel 12 such that an attempt to thread the collar 20 onto the medical connector 30 will result in the free spinning of the collar 20 relative to the barrel 12 thereby preventing connection to the medical connector 30 and reuse of the syringe 10. In other words, the barrel 12 may be rotated in a clockwise direction, but, due to friction between the medical connector 30 and the collar 20, the collar 20 and the medical connector 30 will remain stationary while the barrel 12 spins. Without movement of the collar 20 relative to the medical connector 30, the collar 20 cannot be secured to the medical connector 30. As discussed above, in some aspects or embodiments, the axial movement of the collar 20 to the reuse prevention position may assist or solely contribute to the medical connector 30 being unable to reconnect to the barrel 12.

Elements of one disclosed aspect can be combined with elements of one or more other disclosed aspects to form different combinations, all of which are considered to be within the scope of the present invention.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A syringe comprising:

a barrel having a first end and a second end positioned opposite from the first end, the barrel defining an interior space;

a stopper positioned within the interior space, the stopper is moveable within the interior space relative to the barrel;

a plunger connected to the stopper; and a collar comprising threads configured to engage corresponding threads of a medical connector, the collar at least partially received by the barrel, one of the barrel and the collar defining a slot and the other of the barrel and the collar comprising a pin received within the slot, wherein the collar has a connection position where the collar is fixed relative to the barrel when the syringe is being connected to the medical connector, a disconnection position where the collar is fixed relative to the barrel when the syringe is being disconnected from the medical connector, and a reuse prevention position where the collar is rotatable relative to the barrel.

2. The syringe of claim 1, wherein the barrel defines the slot and the slot comprises a connection portion having a first end and a second end and a reuse prevention portion extending from the connection portion, wherein the pin is positioned at the first end of the connection portion of the slot and engaged with the barrel when the collar is in the connection position, wherein the pin is positioned at the second end of the connection portion of the slot and engaged with the barrel when the collar is in the disconnection position, and wherein the pin is positioned within the reuse prevention portion of the slot when the collar is in the reuse prevention position.

3. The syringe of claim 2, wherein the reuse prevention portion of the slot extends 360 degrees.

4. The syringe of claim 2, wherein the slot comprises a transition portion extending between the connection portion and the reuse prevention portion of the slot.

5. The syringe of claim 2, wherein the barrel comprises a protrusion extending into the connection portion of the slot, and wherein the protrusion is configured to allow movement of the pin from the first end of the connection portion of the slot to the second end of the connection portion of the slot and prevent movement of the pin from the second end of the connection portion of the slot to the first end of the connection portion of the slot.

6. The syringe of claim 5, wherein the protrusion is configured to guide the pin toward the reuse prevention portion of the slot.

7. The syringe of claim 5, wherein the connection portion of the slot extends in a radial direction relative to a longitudinal axis of the barrel, and wherein the protrusion is flexible and extends into the connection portion of the slot in a direction extending from the first end of the connection portion of the slot toward the second end of the connection portion of the slot.

8. The syringe of claim 1, wherein the collar is configured to move axially toward the second end of the barrel when the collar moves from the disconnection position to the reuse prevention position.

9. The syringe of claim 1, wherein the barrel defines the slot and the collar comprises the pin.

10. The syringe of claim 9, wherein the barrel defines an opening extending from the first end of the barrel to the slot, the opening configured to receive the pin during assembly of the collar within the barrel.

11. The syringe of claim 10, wherein the opening comprises a narrowed portion, and wherein the pin is configured to widen the opening when the pin engages the narrowed portion and subsequently return to an original position when the pin enters the slot.

12. The syringe of claim 10, further comprising a cap positioned on the first end of the barrel, wherein the cap comprises an extension received within the opening of the barrel to secure the cap to the barrel.

13. The syringe of claim 1, wherein an inner surface of the collar comprises the threads.

14. The syringe of claim 13, wherein the barrel comprises a male luer received within the collar.

15. A syringe comprising:

a barrel having a first end and a second end positioned opposite from the first end, the barrel defining an interior space;

a stopper positioned within the interior space, the stopper is moveable within the interior space relative to the barrel;

a plunger connected to the stopper; and a collar comprising threads configured to engage corresponding threads of a medical connector, the collar at least partially received by the barrel, one of the barrel and the collar defining a slot and the other of the barrel and the collar comprising a pin received within the slot, wherein the collar has a connection position where the collar is fixed relative to the barrel when the syringe is being connected to the medical connector, a disconnection position where the collar is fixed relative to the barrel when the syringe is being disconnected from the medical connector, and a reuse prevention position wherein the collar is axially spaced from the first end of the barrel to prevent the threads of the collar from engaging with the threads of the medical connector.

* * * * *